US008409191B2

(12) United States Patent
Avitall et al.

(10) Patent No.: US 8,409,191 B2
(45) Date of Patent: Apr. 2, 2013

(54) PRESHAPED ABLATION CATHETER FOR ABLATING PULMONARY VEIN OSTIA WITHIN THE HEART

(75) Inventors: Boaz Avitall, Milwaukee, WI (US); Joe Koblish, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1953 days.

(21) Appl. No.: 10/983,072

(22) Filed: Nov. 4, 2004

(65) Prior Publication Data

US 2006/0095030 A1    May 4, 2006

(51) Int. Cl.
    *A61B 18/14*      (2006.01)
(52) U.S. Cl. ........................ 606/41; 604/95.04
(58) Field of Classification Search .................... 606/41, 606/45–50; 607/101, 102, 122; 604/95.04; 600/374
See application file for complete search history.

(56) References Cited

U.S. PATENT DOCUMENTS

| | | | |
|---|---|---|---|
| 30,729 | A | 11/1860 | Graves |
| 865,331 | A | 9/1907 | Coldwell |
| 949,408 | A | 2/1910 | Anderson |
| 4,650,466 | A | 3/1987 | Luther |
| 4,706,671 | A | 11/1987 | Weinrib |
| 4,882,777 | A | 11/1989 | Narula |
| 4,921,484 | A | 5/1990 | Hillstead |
| 5,156,151 | A | 10/1992 | Imran |
| 5,228,442 | A | 7/1993 | Imran |
| 5,239,999 | A | 8/1993 | Imran |
| 5,263,493 | A | 11/1993 | Avitall |
| 5,279,299 | A | 1/1994 | Imran |
| 5,327,885 | A | 7/1994 | Griffith |

(Continued)

FOREIGN PATENT DOCUMENTS

| | | |
|---|---|---|
| EP | 0 670 168 A1 | 11/1994 |
| EP | 0 670 168 A1 | 9/1995 |

(Continued)

OTHER PUBLICATIONS

PCT International Search Report for PCT/US2005/039785, Applicant: Boston Scientific Scimed, Inc., Form PCT/ISA/210 and 220, dated Mar. 20, 2006 (6 pages).

(Continued)

*Primary Examiner* — Michael Peffley
(74) *Attorney, Agent, or Firm* — Seager, Tufte & Wickhem, LLC

(57) ABSTRACT

Catheters and methods are provided for performing medical procedures, such as tissue ablation, adjacent the ostia of anatomical vessels, such as pulmonary veins. The catheter comprises an elongated flexible integrated catheter body having proximal and distal shaft portions and at least one operative element carried by the distal shaft portion. The distal shaft portion has a proximal section configured to be internally actuated (e.g., using a steering mechanism or pre-shaping the proximal section) to form a simple curve with an apex that can be inserted into the vessel ostium, an intermediate section pre-shaped to form a curve that bends opposite the simple curve, and a distal section configured to be placed into a non-radial relationship (tangential or oblique) with the vessel ostium when the apex of the simple curve is inserted into the vessel ostium. By this arrangement, the operative element is configured to be placed firmly in contact with tissue at a predefined radial location relative to the vessel ostium when the apex of the simple curve is inserted into the vessel ostium.

40 Claims, 9 Drawing Sheets

U.S. PATENT DOCUMENTS

| | | | |
|---|---|---|---|
| 5,368,567 | A | 11/1994 | Lee |
| 5,383,874 | A | 1/1995 | Jackson et al. |
| 5,391,199 | A | 2/1995 | Ben-Haim |
| 5,411,546 | A | 5/1995 | Bowald et al. |
| 5,423,772 | A | 6/1995 | Lurie et al. |
| 5,456,667 | A | 10/1995 | Ham et al. |
| 5,456,682 | A | 10/1995 | Edwards et al. |
| 5,505,730 | A | 4/1996 | Edwards |
| 5,571,038 | A | 11/1996 | Halling |
| 5,582,609 | A | 12/1996 | Swanson et al. |
| 5,617,854 | A * | 4/1997 | Munsif .................... 600/374 |
| 5,702,368 | A | 12/1997 | Stevens et al. |
| 5,733,280 | A | 3/1998 | Avitall |
| 5,738,683 | A | 4/1998 | Osypka |
| 5,755,715 | A | 5/1998 | Stern et al. |
| 5,814,028 | A * | 9/1998 | Swartz et al. .................. 604/528 |
| 5,820,591 | A | 10/1998 | Thompson et al. |
| 5,823,955 | A * | 10/1998 | Kuck et al. .................... 600/374 |
| 5,916,214 | A | 6/1999 | Cosio et al. |
| 5,938,660 | A | 8/1999 | Swartz et al. |
| 5,938,694 | A | 8/1999 | Jaraczewski et al. |
| 5,971,983 | A | 10/1999 | Lesh |
| 5,972,019 | A | 10/1999 | Engelson et al. |
| 5,983,126 | A | 11/1999 | Wittkampf |
| 5,991,650 | A | 11/1999 | Swanson et al. |
| 5,993,462 | A | 11/1999 | Pomeranz et al. |
| 6,002,955 | A * | 12/1999 | Willems et al. ................ 600/374 |
| 6,012,457 | A | 1/2000 | Lesh |
| 6,024,740 | A | 2/2000 | Lesh et al. |
| 6,029,671 | A | 2/2000 | Stevens et al. |
| 6,064,902 | A | 5/2000 | Haissaguerre et al. |
| 6,066,126 | A | 5/2000 | Li et al. |
| 6,068,629 | A | 5/2000 | Haissaguerre et al. |
| 6,071,279 | A | 6/2000 | Whayne et al. |
| 6,090,474 | A | 7/2000 | Johansson et al. |
| 6,106,522 | A | 8/2000 | Fleischman et al. |
| 6,164,283 | A | 12/2000 | Lesh |
| 6,214,002 | B1 | 4/2001 | Fleischman et al. |
| 6,224,587 | B1 | 5/2001 | Gibson |
| 6,237,605 | B1 | 5/2001 | Vaska et al. |
| 6,270,496 | B1 * | 8/2001 | Bowe et al. .................... 606/41 |
| 6,287,301 | B1 | 9/2001 | Thompson et al. |
| 6,311,692 | B1 | 11/2001 | Vaska et al. |
| 6,325,797 | B1 | 12/2001 | Stewart et al. |
| 6,464,700 | B1 | 10/2002 | Koblish et al. |
| 6,485,489 | B2 | 11/2002 | Teirstein et al. |
| 6,490,474 | B1 | 12/2002 | Willis et al. |
| 6,529,756 | B1 | 3/2003 | Phan et al. |
| 6,542,781 | B1 | 4/2003 | Koblish et al. |
| 6,572,611 | B1 | 6/2003 | Falwell |
| 6,572,612 | B2 | 6/2003 | Stewart et al. |
| 6,628,976 | B1 * | 9/2003 | Fuimaono et al. ............ 600/374 |
| 6,645,199 | B1 | 11/2003 | Jenkins et al. |
| 6,652,515 | B1 | 11/2003 | Maguire et al. |
| 6,728,563 | B2 | 4/2004 | Rashidi |
| 6,733,499 | B2 | 5/2004 | Scheib |
| 6,745,080 | B2 | 6/2004 | Koblish |
| 6,869,414 | B2 * | 3/2005 | Simpson et al. ........... 604/95.04 |
| 6,887,236 | B2 | 5/2005 | Gilboa |
| 6,923,808 | B2 | 8/2005 | Taimisto |
| 6,926,669 | B1 | 8/2005 | Stewart et al. |
| 6,926,714 | B1 | 8/2005 | Sra |
| 6,950,689 | B1 | 9/2005 | Willis et al. |
| 6,973,339 | B2 | 12/2005 | Govari |
| 7,013,619 | B2 | 3/2006 | Hoover |
| 7,101,362 | B2 * | 9/2006 | Vanney .......................... 604/523 |
| 2001/0007070 | A1 | 7/2001 | Stewart et al. |
| 2001/0039413 | A1 | 11/2001 | Bowe |
| 2003/0069570 | A1 | 4/2003 | Witzel et al. |
| 2003/0093072 | A1 | 5/2003 | Friedman |
| 2003/0114833 | A1 | 6/2003 | Thompson et al. |
| 2003/0130598 | A1 | 7/2003 | Manning et al. |
| 2003/0208102 | A1 | 11/2003 | Gilboa |
| 2004/0034365 | A1 | 2/2004 | Lentz et al. |
| 2004/0106920 | A1 | 6/2004 | Jenkins et al. |
| 2004/0147827 | A1 | 7/2004 | Bowe |
| 2005/0004516 | A1 | 1/2005 | Vanney |
| 2005/0070887 | A1 | 3/2005 | Taimisto et al. |
| 2005/0187455 | A1 * | 8/2005 | Rashidi .......................... 600/374 |
| 2005/0197623 | A1 | 9/2005 | Leeflang et al. |
| 2005/0222557 | A1 | 10/2005 | Baxter et al. |
| 2006/0095030 | A1 | 5/2006 | Avitall et al. |
| 2006/0241366 | A1 * | 10/2006 | Falwell et al. ................ 600/374 |

FOREIGN PATENT DOCUMENTS

| | | |
|---|---|---|
| EP | 0 898 480 | 3/1999 |
| WO | WO 93/15790 | 8/1993 |
| WO | WO 95/08364 | 3/1995 |
| WO | WO 97/26038 | 7/1997 |
| WO | WO 99/56810 | 11/1999 |
| WO | WO 00/32129 | 6/2000 |
| WO | WO 01/03766 | 1/2001 |
| WO | WO 01/87174 | 11/2001 |
| WO | WO 2004/032791 A2 | 4/2004 |
| WO | WO 2006/012668 | 2/2006 |

OTHER PUBLICATIONS

PCT Written Opinion of the International Search Authority for PCT/US2005/039785, Applicant: Boston Scientific Scimed, Inc., Form PCT/ISA/237, dated Mar. 20, 2006 (5 pages).

PCT International Search Report for PCT/US2006/017511, Boston Scientific Scimed, Inc., Form PCT/ISA/210 and 220, dated Sep. 12, 2006 (7 pages).

PCT Written Opinion of the International Search Authority for PCT/US2006/017511, Boston Scientific Scimed, Inc., Form PCT/ISA/237, dated Sep. 12, 2006 (7 pages).

PCT International Search Report for PCT/US2006/017457, Boston Scientific Scimed, Inc., Form PCT/ISA/210 and 220, dated Sep. 25, 2006 (6 pages).

PCT Written Opinion of the International Search Authority for PCT/US2006/017457, Boston Scientific Scimed, Inc., Form PCT/ISA/237, dated Sep. 25, 2006 (5 pages).

PCT International Preliminary Report for PCT/US2005/039785, Boston Scientific Scimed, Inc., Form PCT/IB/373 and PCT/ISA/237, dated May 8, 2007, (6 pages).

PCT International Preliminary Report for PCT/US2006/017457, Boston Scientific Scimed, Inc., Form PCT/IB/373 and PCT/ISA/237, dated Nov. 6, 2007, (6 pages).

PCT International Preliminary Report for PCT/US2006/017511, Boston Scientific Scimed, Inc., Form PCT/IB/373 and PCT/ISA/237, dated Nov. 15, 2007, (9 pages).

Office Action dated Nov. 10, 2008 for U.S. Appl. No. 11/429,051, filed May 5, 2005, Boaz Avitall, (23 pages).

Office Action dated Nov. 14, 2008 for U.S. Appl. No. 11/418,757, filed May 5, 2005, Boaz Avitall, (21 pages).

Office Action dated Apr. 4, 2009 in U.S. Appl. No. 11/418,757, filed May 5, 2006, Boaz Avitall, (15 pages).

Office Action dated Sep. 15, 2009 in U.S. Appl. No. 11/418,757, filed May 5, 2006, Boaz Avitall, (26 pages).

Office Action dated Apr. 17, 2009 in U.S. Appl. No. 11/429,051, filed May 5, 2006, Boaz Avitall, (18 pages).

Office Action dated May 14, 2012 in Japanese Patent Application No. 2007-539338, Boston Scientific Limited, (2pages) including an English Translations provided by Shusaku Yamamoto (2pages).

Office Action dated Oct. 28, 2011 in Japanese Patent Application No. 2007-539338, Boston Scientific Limited, (2pages) including an English Translations provided by Shusaku Yamamoto (2pages).

Office Action dated Jun. 22, 2011 in Japanese Patent Application No. 2007-539338, Boston Scientific Limited, (2pages) including an English Translations provided by Shusaku Yamamoto (3pages).

Office Action dated Jul. 7, 2010 in European Patent Application No. 05 824 866.7-1526, Boston Scientific Limited (4pages).

Office Action dated Oct. 24, 2011 in Canadian Patent Application No. 2584549, Boston Scientific Limited (2pages).

Office Action dated Jun. 1, 2011 in Australian Patent Application No. 2005304983, Boston Scientific Limited (5pages).

Office Action dated Jul. 26, 2010 in Australian Patent Application No. 2005304983, Boston Scientific Limited (5pages).

Office Action dated Mar. 2, 2012 in Japanese Patent Application No. 2008-510289, Boston Scientific Limited, (2pages) including an English Translations provided by Shusaku Yamamoto (3pages).

Office Action dated Jun. 8, 2011 in Japanese Patent Application No. 2008-510289, Boston Scientific Limited, (3pages) includling an English Translations provided by Shusaku Yamamoto (4pages).

Office Action dated May 31, 2011 in European Patent Application No. 06 759 200.6-1526, Boston Scientific Limited, (6pages).

Office Action dated Aug. 4, 2009 in European Patent Application No. 06 759 200.6-1526, Boston Scientific Limited, (4pages).

Reply Brief dated Apr. 5, 2012 in U.S. Appl. No. 11/418,757, Boaz Avitall, (13pages).

Examiner's Answer dated Feb. 29, 2012 in U.S. Appl. No. 11/418,757, Boaz Avitall, (29pages).

Appeal Brief dated Jan. 4, 2012 in U.S. Appl. No. 11/418,757, Boaz Avitall, (35pages).

Advisory Action dated Oct. 24, 2011 in U.S. Appl. No. 11/418,757, Boaz Avitall, (4pages).

Office Action dated Aug. 1, 2011 in U.S. Appl. No. 11/418,757, Boaz Avitall, (26pages).

Math Made Nice-N-Easy, 8, Piscataway, NJ: Research & Education Association, 2002, 3, eBook (3pages).

Office Action dated May 9, 2011 in U.S. Appl. No. 11/418,757, Boaz Avitall, (32pages).

Office Action dated Dec. 21, 2010 in U.S. Appl. No. 11/418,757, Boaz Avitall, (29pages).

Advisory Action dated Feb. 16, 2010 in U.S. Appl. No. 11/418,757, Boaz Avitall, (4pages).

Office Action dated Nov. 30, 2009 in U.S. Appl. No. 11/418,757, Boaz Avitall, (23pages).

Reply Brief dated Apr. 12, 2011 in U.S. Appl. No. 11/429,051, Boaz Avitall, (7pages).

Examiner's Answer dated Feb. 15, 2011 in U.S. Appl. No. 11/429,051, Boaz Avitall, (15pages).

Supplemental Appeal Brief dated Dec. 1, 2010 in U.S. Appl. No. 11/429,051, Boaz Avitall, (21pages).

Appeal Brief dated Nov. 22, 2010 in U.S. Appl. No. 11/429,051, Boaz Avitall, (20pages).

Office Action dated Mar. 4, 2010 in U.S. Appl. No. 11/429,051, Boaz Avitall, (13pages).

Office Action dated Nov. 9, 2009 in U.S. Appl. No. 11/429,051, Boaz Avitall, (22pages).

* cited by examiner

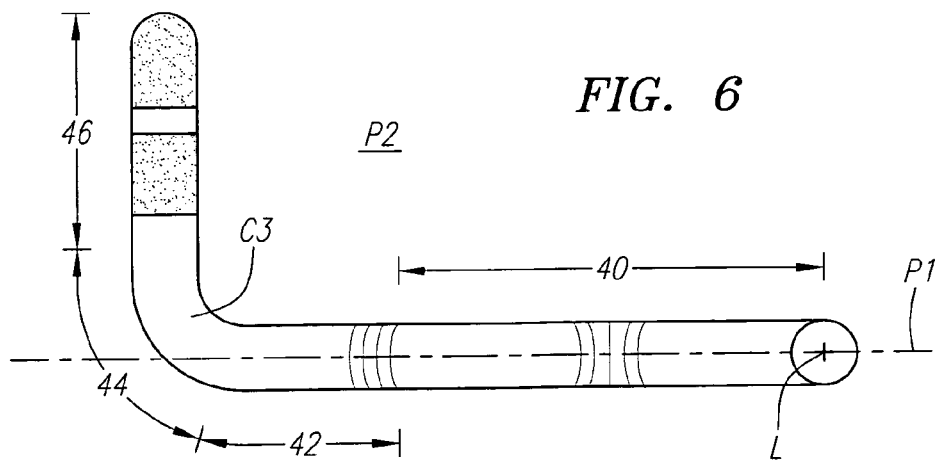
FIG. 6
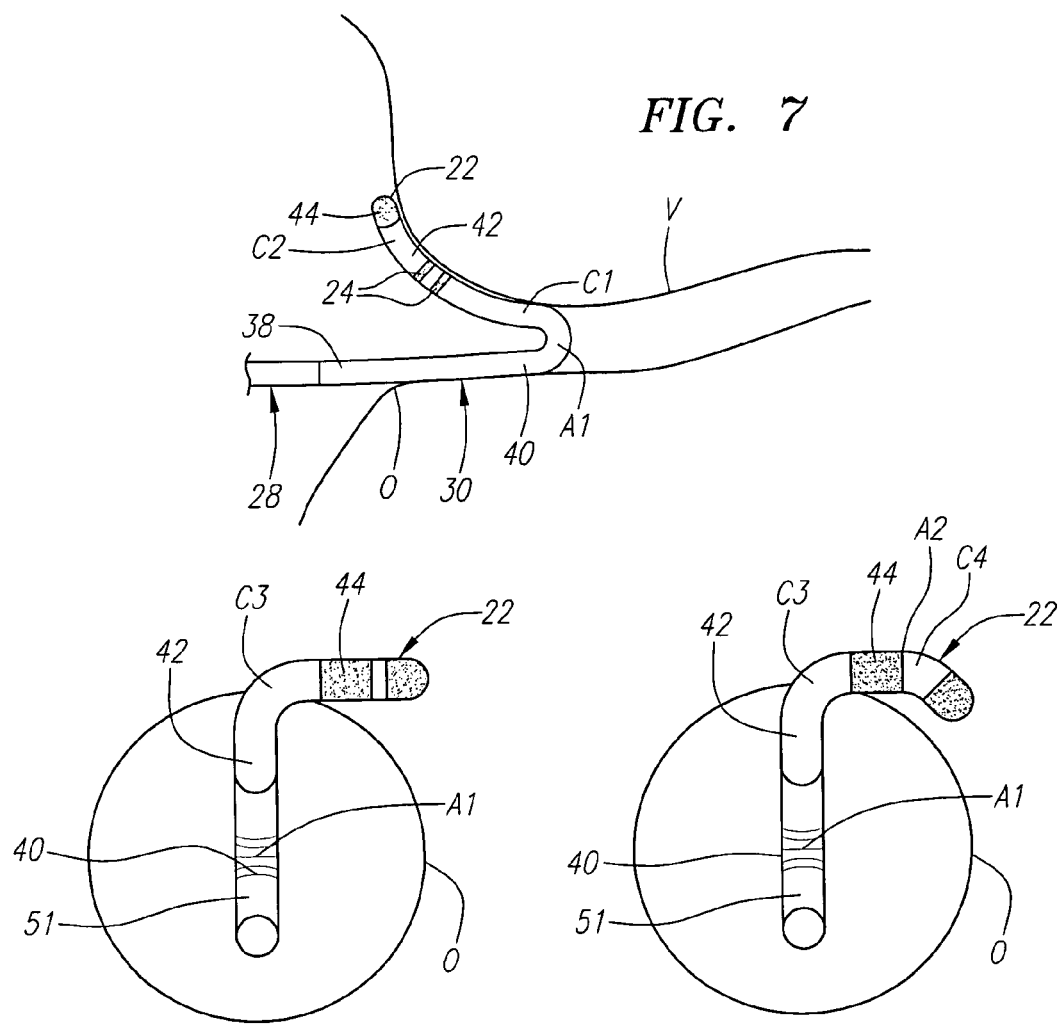
FIG. 7
FIG. 8
FIG. 9

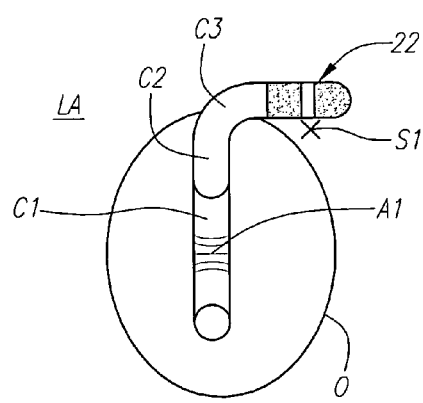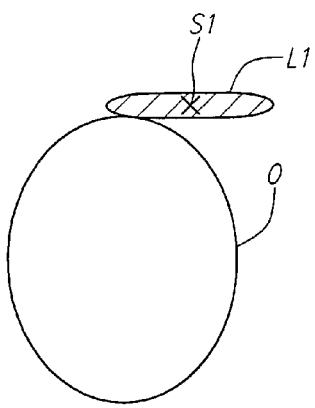
*FIG. 16D*  *FIG. 16E*
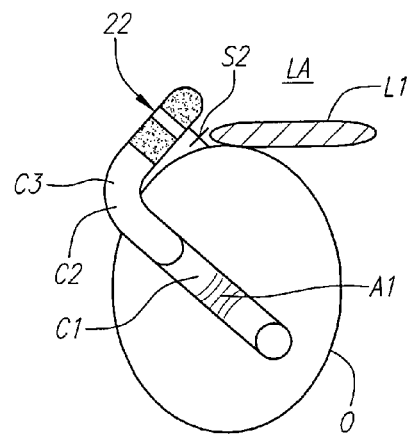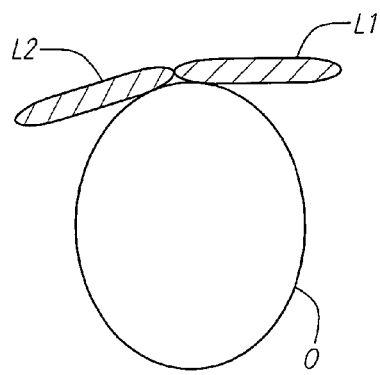
*FIG. 16F*  *FIG. 16G*

PRESHAPED ABLATION CATHETER FOR ABLATING PULMONARY VEIN OSTIA WITHIN THE HEART

FIELD OF THE INVENTION

The present inventions generally relate to systems and methods for treating tissue, and more particularly to systems and methods for ablating tissue in and around the ostia of vessels, such as pulmonary veins, and other anatomical openings.

BACKGROUND OF THE INVENTION

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized manner to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure," which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, not only is the maze procedure is technically difficult to do, it also requires open heart surgery and is very expensive.

Maze-like procedures have also been developed utilizing electrophysiology procedures, which involves forming lesions on the endocardium (the lesions being 1 to 15 cm in length and of varying shape) using an ablation catheter to effectively create a maze for electrical conduction in a predetermined path. The formation of these lesions by soft tissue coagulation (also referred to as "ablation") can provide the same therapeutic benefits that the complex incision patterns of the surgical maze procedure presently provides, but without invasive, open heart surgery.

In certain advanced electrophysiology procedures, it is desirable to create a lesions around, within, or otherwise adjacent to orifices. For example, as part of the treatment for certain categories of atrial fibrillation, it may be desirable to create a curvilinear lesion around or within the ostia of the pulmonary veins (PVs), and a linear lesion connecting one or more of the PVs to the mitral valve annulus. Preferably, such curvilinear lesion is formed as far out from the PVs as possible to ensure that the conduction blocks associated with the PVs are indeed electrically isolated from the active heart tissue. To do this, a physician must be able to move the ablation catheter tip along a desired path and either deliver ablative energy while slowly dragging the tip along the path, or deliver energy at a number of discrete points along that path. Either way, it is crucial that the physician be able to accurately and controllably move the catheter tip along that path. When ablating around the PVs, however, energy is typically applied along the curvilinear path using a free-hand approach, thereby rendering it difficult to accurately move the catheter tip along that path. More importantly, during the electrophysiology procedure, it is important to prevent inadvertent damage to non-targeted regions, such as the PVs themselves, which could produce stenosis of the PVs. Thus, it has proven difficult to form circumferential lesions using conventional devices to isolate the PVs and cure ectopic atrial fibrillation.

Accordingly, there remains a need to be able to more efficiently and accurately create circumferential lesions around bodily orifices, such as the ostia of the PVs.

SUMMARY OF THE INVENTION

In accordance with a first aspect of the present inventions, a catheter is provided. The catheter comprises an elongated flexible catheter body and at least one operative element (e.g., a tissue ablative element or diagnostic element). The catheter body includes a proximal shaft portion and a distal shaft portion that are integrated together (i.e., the proximal and distal shaft portions do not slide relative to each other in the same manner that a guide sheath and slidable catheter would). The proximal and distal shaft portions can, e.g., be separately formed proximal and distal members that are subsequently integrated together, e.g., via bonding, or can be topological sections of a unibody catheter body.

In either event, the distal shaft portion has a proximal section configured to be internally actuated from a straight geometry to a simple curve (i.e., a curve that lies substantially in a single plane). For example, the catheter can comprise a steering mechanism that is operable to internally actuate the proximal section to form the simple curve, or the proximal section can be pre-shaped to form the simple curve in the absence of an external force, such as gravity or the constraining force apply by a guide sheath. The simple curve bends more than 70 degrees, preferably at least 90 degrees, and more preferably at least 135 degrees, so that, e.g., its apex can be more easily inserted into an ostium of a vessel (e.g., a pulmonary vein ostium). To further facilitate insertion into a vessel ostium, the simple curve may be eccentric, with its apex having the smallest radius curvature of the simple curve. In one embodiment, the proximal section of the distal shaft portion is radio-opaque, so that, e.g., the extent to which the simple curve is inserted into the vessel ostium can be conveniently determined based on the angle formed by the simple curve bending about its apex.

The distal shaft portion further includes an intermediate section pre-shaped to form a complex curve that bends opposite to and out-of-plane with the simple curve. In one embodiment, the complex curve has a: 1) proximal curve that, when projected onto a plane of the simple curve, bends at least 90 degrees, and preferably within the range of 90 to 135 degrees; and 2) and a distal curve that, when projected onto a plane perpendicular to the longitudinal axis of the proximal shaft portion, bends in the range of 60 degrees to 120 degrees, and preferably approximately 90 degrees.

The distal shaft portion further includes a distal section on which the operative element(s) is mounted, which in one embodiment, forms the distal tip of the catheter body. The distal section may be substantially straight, but can also be pre-shaped to form a simple curve with an apex that points away from the longitudinal axis of the proximal shaft portion. Either configuration lends itself well when linear ablative elements are used, so that a linear ablation can be more efficiently placed around the vessel ostium. The distal shaft portion may optionally include a substantially straight shaft transition section between the proximal shaft portion and the proximal section of the distal shaft portion. Preferably, the proximal shaft portion and shaft transition section are collinear to facilitate the pushability of the catheter (i.e., to minimize the chance that the distal shaft portion will collapse onto the proximal shaft portion in the presence of a resistive axial force, which may otherwise occur if the proximal shaft portion and shaft transition section were angled relative to each other).

In one embodiment, the catheter is designed to be used within the ostium of a pulmonary vein. In this case, the smallest radius of curvature of the simple curve is within the range of 1.25 to 2.50 centimeters, and the smallest radius of curvature of the complex curve is within the range of 1.25 to 3.75 centimeters. The proximal section has a length within the range of 2.50 to 6.50 centimeters, the intermediate section has a length within the range of 0.50 to 2.00 centimeters, and distal section has a length within the range of 0.50 to 2.00 centimeters.

In accordance with a second aspect of the present inventions, a catheter is provided. Like the previously described catheter, the catheter in this case comprises an elongated flexible integrated catheter body having proximal and distal shaft portions and at least one operative element carried by the distal shaft portion. The distal shaft portion has a proximal section configured to be internally actuated (e.g., using a steering mechanism or pre-shaping the proximal section) to form a simple curve with an apex that can be inserted into an ostium of an anatomical vessel, an intermediate section pre-shaped to form a curve that bends opposite the simple curve, and a distal section configured to be placed into a non-radial relationship (tangential or oblique) with the vessel ostium when the apex of the simple curve is inserted into the vessel ostium. By this arrangement, the operative element(s), which may be of the same nature as those described above, is configured to be placed firmly in contact with tissue adjacent the vessel ostium when the apex of the simple curve is inserted into the vessel ostium.

In accordance with a third aspect of the present inventions, a method of performing a medical procedure adjacent an ostium of a vessel using either of the previously described catheters is provided. The method comprises inserting the apex of the simple curve into the vessel ostium to place the operative element(s) in contact with a first tissue site adjacent the vessel ostium, and performing the medical procedure on the first tissue site with the operative element(s). In one method, the simple curve is rotated within the vessel ostium about the apex to place the operative element in contact with a second tissue site adjacent the vessel ostium, and the medical procedure is then performed on the second tissue site with the operative element(s). This method lends itself well to ablation procedures, in which case, the operative element(s) comprises an ablative element, and the performance of the medical procedure comprises forming a lesion at the first and/or second tissue sites with the ablative element.

In accordance with a fourth aspect of the present inventions, a method of performing a medical procedure adjacent an anatomical vessel (such as a pulmonary vein) using a catheter is provided. The catheter has a curvable section and an operative element distal to the curved section. The method comprises forming the curvable section into a curve having an apex. This can be accomplished, e.g., by using a steering mechanism or by pre-shaping the curvable section and removing a sheath from the curvable section. The method further comprises inserting the apex within the vessel ostium to place the ablative element in contact with a first tissue site adjacent the vessel ostium, performing the medical procedure on the first tissue site with the operating element, rotating the curve within the vessel ostium about the apex to place the operative element in contact with a second tissue site adjacent the vessel ostium, and then performing a medical procedure on the second tissue site with the operative element. Notably, because the curve is rotated around a fixed point (i.e., the apex), the medical procedure can be performed around the vessel ostium in a controlled and predefined manner.

This method lends itself well to the medical procedures that involve forming lesions around vessel ostia, and in particular, pulmonary vein ostia, where control of the ablation process is crucial. The lesions can be created for any purpose, but the method lends itself well to therapeutic procedures involving the electrical isolation of arrhythmia causing substrates from the left atrium of the heart. The lesions can either be discrete or can form a continuous lesion, but preferably, are linear or curvilinear, and somewhat tangential, to maximize the span of the lesions about the ostium and the effectiveness of the lesions in blocking the errant electrical pathways from the pulmonary vein. In one method, the lesion formation and rotation steps are performed until a plurality of lesions are circumferentially disposed about the vessel ostium.

Other features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 6 is another profile view of the distal end of the ablation/mapping catheter of FIG. 2;

FIG. 7 is a side view of the distal end of the ablation/mapping catheter of FIG. 2, particularly shown inserted into the ostium of a pulmonary vein;

FIG. 8 is a front view of the distal end of the ablation/mapping catheter of FIG. 2, particularly shown inserted into the ostium of a pulmonary vein;

FIG. 9 is a front view of the distal end of an alternative ablation/mapping catheter that can be used in the tissue ablation system of FIG. 2, particularly shown inserted into the ostium of a pulmonary vein;

FIGS. 16A-16G are plan views of a method of using the tissue treatment system of FIG. 1 to create a circumferential lesion around the ostium of a pulmonary vein.

DETAILED DESCRIPTION OF THE PREFERRED EMBODIMENTS

Figure 1:
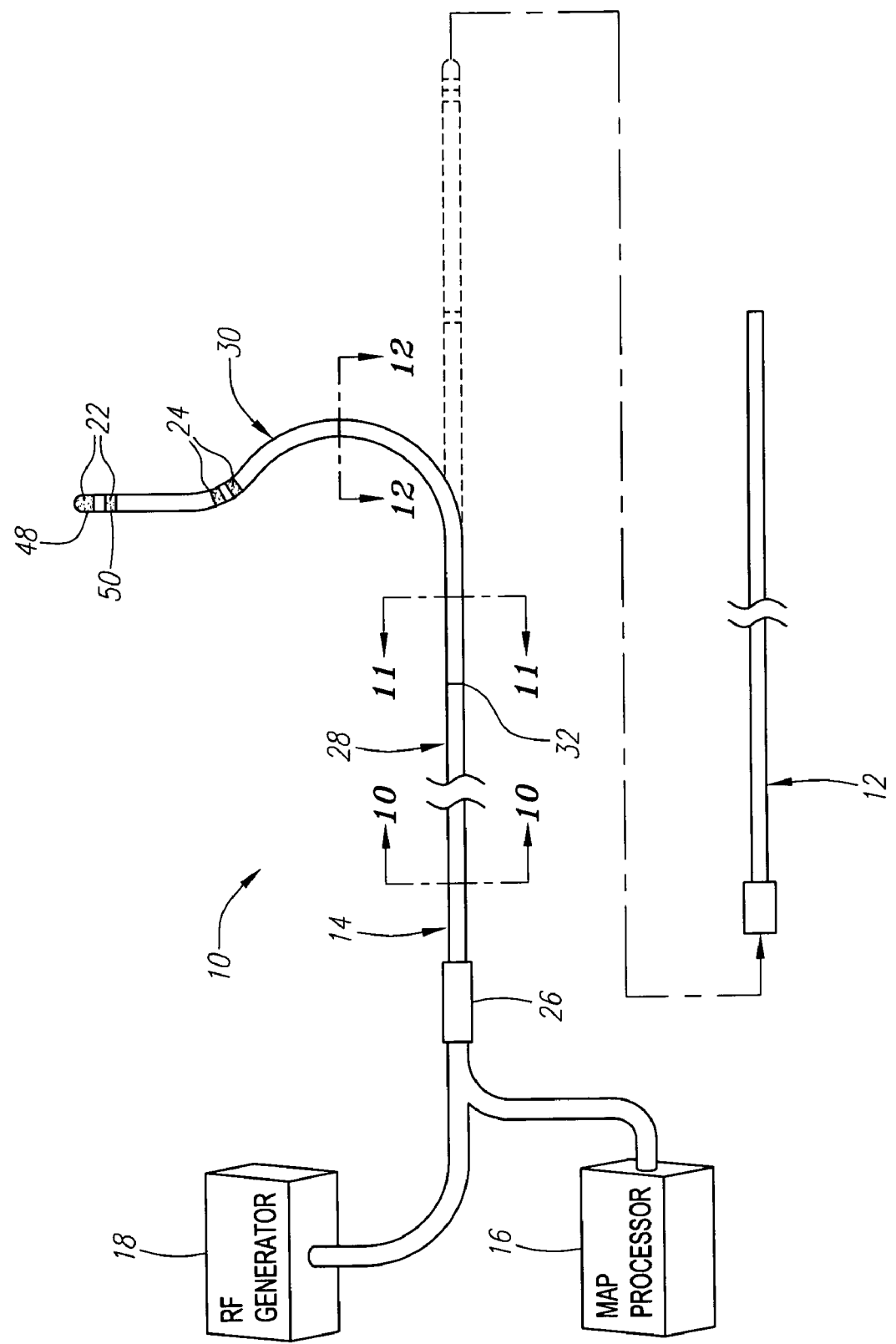
FIG. 1 is a plan view of one preferred embodiment of a tissue ablation system constructed in accordance with the present inventions.

Referring to FIG. 1, an exemplary tissue ablation system 10 constructed in accordance with the present inventions is shown. The system 10 may be used within body lumens, chambers or cavities for therapeutic and diagnostic purposes in those instances where access to interior bodily regions is obtained through, for example, the vascular system or alimentary canal and without complex invasive surgical procedures. For example, the system 10 has application in the diagnosis and treatment of arrhythmia conditions within the heart. The system 10 also has application in the treatment of ailments of the gastrointestinal tract, prostrate, brain, gall bladder, uterus, and other regions of the body. As an example, the system 10 will be described hereinafter for use in pulmonary veins, and specifically, to electrically isolate one or more arrhythmia causing substrates within the ostium of a pulmonary vein from the left atrium of the heart in order to treat ectopic atrial fibrillation.

The system 10 generally comprises a conventional guide sheath 12 and an ablation/mapping catheter 14 that can be guided through the guide sheath 12. As will be described in further detail below, the ablation/mapping catheter 14 is configured to be introduced through the vasculature of the patient, and into the left atrium of the heart, where it can be used to ablate and map heart tissue within and/or around the ostia of selected pulmonary veins. The system 10 also comprises a mapping processor 16 and a source of ablation energy, and in particular, a radio frequency (RF) generator 18. Although the mapping processor 16 and RF generator 18 are shown as discrete components, they can alternatively be incorporated into a single integrated device.

The mapping processor 16 is configured to detect, process, and record electrical signals within the heart, and specifically, electrical signals adjacent the ostia of the pulmonary vein. Based on these electrical signals, a physician can identify the specific target tissue sites adjacent the pulmonary vein ostia to be ablated, and to ensure that the arrhythmia causing substrates within the pulmonary vein ostia have been electrically isolated by the ablative treatment. Such mapping techniques are well known in the art, and thus for purposes of brevity, will not be described in further detail.

The RF generator 18 is configured to deliver ablation energy to the ablation/mapping catheter 14 in a controlled manner in order to ablate the target tissue sites identified by the mapping processor. Alternatively, other types of ablative sources besides the RF generator 18 can be used, e.g., a microwave generator, an ultrasound generator, a cryoablation generator, and a laser or other optical generator. Ablation of tissue within the heart is well known in the art, and thus for purposes of brevity, the RF generator 18 will not be described in further detail. Further details regarding RF generators are provided in U.S. Pat. No. 5,383,874, which is expressly incorporated herein by reference.

The ablation/mapping catheter 14 may be advanced though the guide sheath 12 to the target location. The sheath 12, which should be lubricious to reduce friction during movement of the ablation/mapping catheter 14, may be advanced over a guidewire in conventional fashion. Alternatively, a steerable sheath may be provided. With respect to materials, the proximal portion of the sheath 12 is preferably a Pebax® material and stainless steel braid composite, and the distal portion is a more flexible material, such as unbraided Pebax®, for steering purposes. The sheath 12 should also be stiffer than the ablation/mapping catheter 14. A sheath introducer (not shown), such as those used in combination with basket catheters, may be used when introducing the ablation/mapping catheter 14 into the sheath 12. The guide sheath 12 preferably includes a radio-opaque compound, such as barium, so that the guide sheath 12 can be observed using fluoroscopic or ultrasound imaging, or the like. Alternatively, a radio-opaque marker (not shown) can be placed at the distal end of the guide sheath 12.

The ablation/mapping catheter 14 comprises an integrated flexible catheter body 20, a plurality of distally mounted operative elements, and in particular, a tissue ablative element 22 and a mapping element 24, and a proximally mounted handle 26. The catheter body 20 comprises a proximal member 28 and a distal member 30 that are preferably either bonded together at an interface 32 with an overlapping thermal bond or adhesively bonded together end to end over a sleeve in what is referred to as a "butt bond." Alternatively, the integrated catheter body 20 may not have separate proximal and distal members 28, 30 that are subsequently integrated together, but instead, may have an unibody design.

Figure 10:
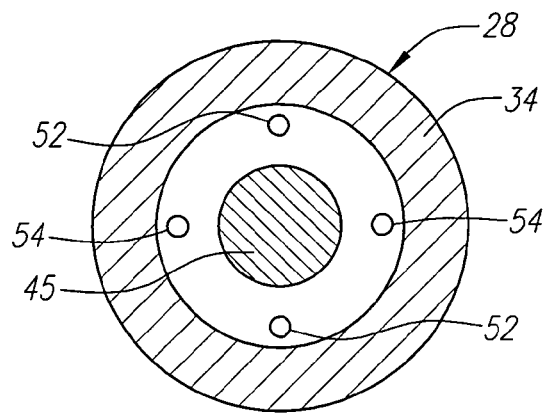
FIG. 10 is a cross-sectional view of the ablation/mapping catheter, taken along the line 10-10 of FIG. 1.
Figure 11:
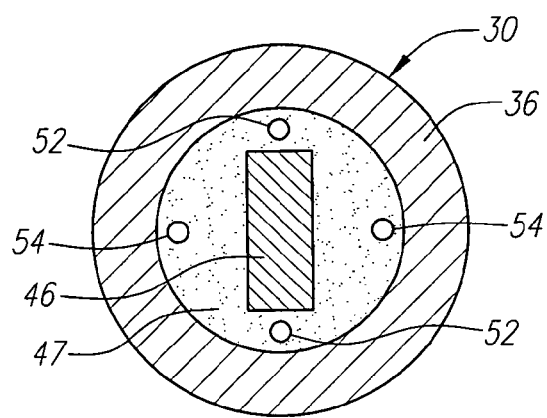
FIG. 11 is a cross-sectional view of the ablation/mapping catheter of FIG. 2, taken along the line 11-11 of FIG. 1.
Figure 12:
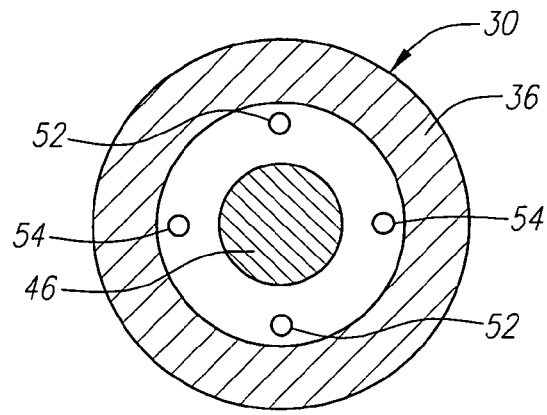
FIG. 12 is a cross-sectional view of the ablation/mapping catheter of FIG. 2, taken along the line 12-12 of FIG. 1.

The catheter body 20 is preferably about 5 French to 9 French in diameter, with the proximal member 28 being relatively long (e.g., 80 to 100 cm), and the distal member 30 relatively short (e.g., 3.5 cm to 10.5 cm). As best illustrated in FIG. 10, the proximal member 28 comprises a tubular body 34 that is preferably formed from a biocompatible thermoplastic material, such as a Pebax® material (polyether block amide) and stainless steel braid composite, which has good torque transmission properties. In some implementations, an elongate guide coil (not shown) may also be provided within the proximal member 28. As best illustrated in FIGS. 11 and 12, the distal member 30 comprises a tubular body 36 that is preferably formed from a softer, more flexible biocompatible thermoplastic material such as unbraided Pebax® material, polyethylene, or polyurethane. The distal member 30 preferably includes a radio-opaque compound, such as barium, so that the catheter body 20 can be observed using fluoroscopic or ultrasound imaging, or the like. Alternatively, radio-opaque markers (not shown) can be placed along the distal member 30.

The catheter body 20 has a resilient shape that facilitates the functionality of the ablation/mapping catheter 14. In particular, and as is standard with most catheters, the proximal member 28 has an unconstrained straight or linear geometry to facilitate the pushability of the ablation/mapping catheter 14 through the guide sheath 12. To this end, the proximal member 28 further comprises a resilient, straight center support 45 positioned inside of and passing through the length of the proximal tubular body 34. In the illustrated embodiment, the proximal center support 45 is a circular element formed from resilient inert wire, such as nickel titanium (commercially available under the trade name nitinol) or 17-7 stainless steel wire. Resilient injection molded plastic can also be used. The diameter of the proximal center support 45 is preferably between about 0.35 mm to 0.80 mm.

Figure 13:
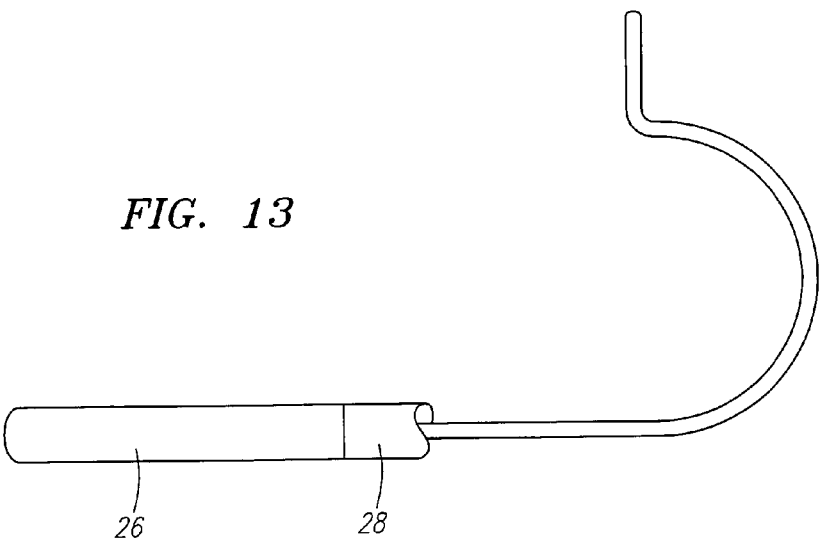
FIG. 13 is a partially cutaway view of the distal end of the ablation/mapping catheter of FIG. 2, particularly showing one means for internally actuating the catheter.

In contrast, the distal member 30 is configured to be alternately placed between a linear geometry (shown in phantom in FIG. 1) and an expanded geometry. The shape of the distal member 30 is achieved through the use of a center support 46 that is positioned inside of and passes through the length of the distal tubular body 36, as illustrated in FIG. 13. In the illustrated embodiment, the distal center support 46 is similar to the proximal center support 45 in composition and dimension. To improve the torqueability of the distal member 30, which is important to the predictable and controlled movement of the distal member 30, the distal center support 46 is preferably affixed within the distal portion of the proximal member 28 (such as by soldering the proximal end of the distal center support 46 to the distal end of the proximal center support 45), so that the torsional force applied to the proximal member 28 is transmitted to the distal member 30 without significant loss. Alternatively, the center supports 45, 46 can be formed of a unibody structure. To further improve the torqueability of the distal member 30, the proximal end of the center support 46 can be flattened into a rectangular cross-sectional geometry, as illustrated in FIG. 11. In addition, a filler material, such as epoxy 47, can be injected into the proximal end of the distal tubular body 36 in order to integrate all of the internal components of the distal member 30 together to further improve the torqueability at the junction between the proximal and distal members 28, 30.

Additional details concerning the placement of a center support within the distal member of a catheter can be found in U.S. Pat. No. 6,287,301, which is expressly incorporated herein by reference. In alternative embodiments, a stylet, instead of the center supports 45, 46, can be used. In this case, the stylet can be removably inserted through a lumen (not shown) formed through the catheter body 20 to place the distal member 30 into its expanded geometry.

Figure 2:
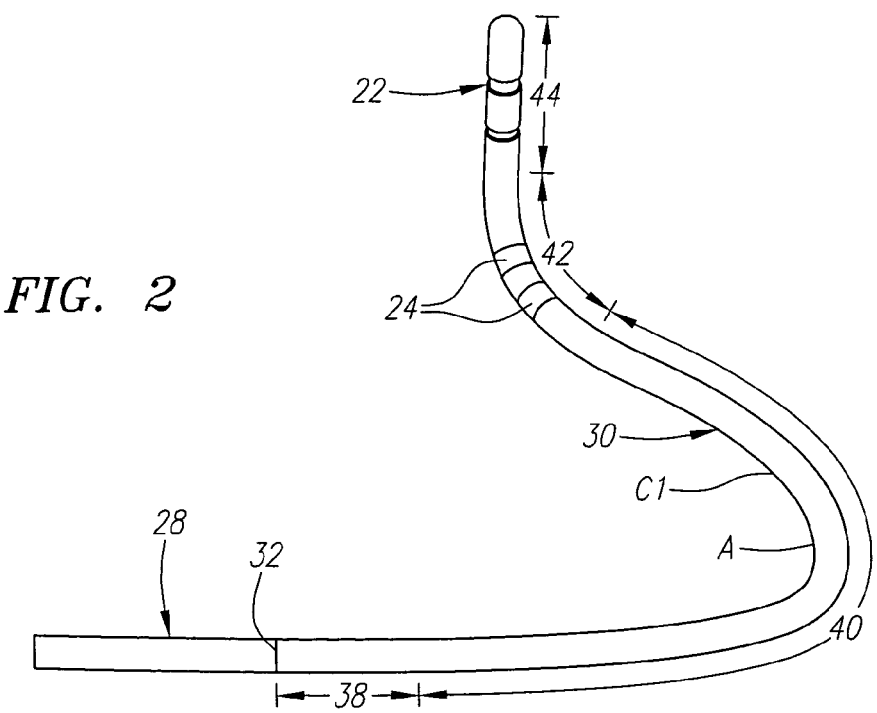
FIG. 2 is a perspective view of the distal end of an ablation/mapping catheter used in the tissue ablation system of FIG. 1.
Figure 3:
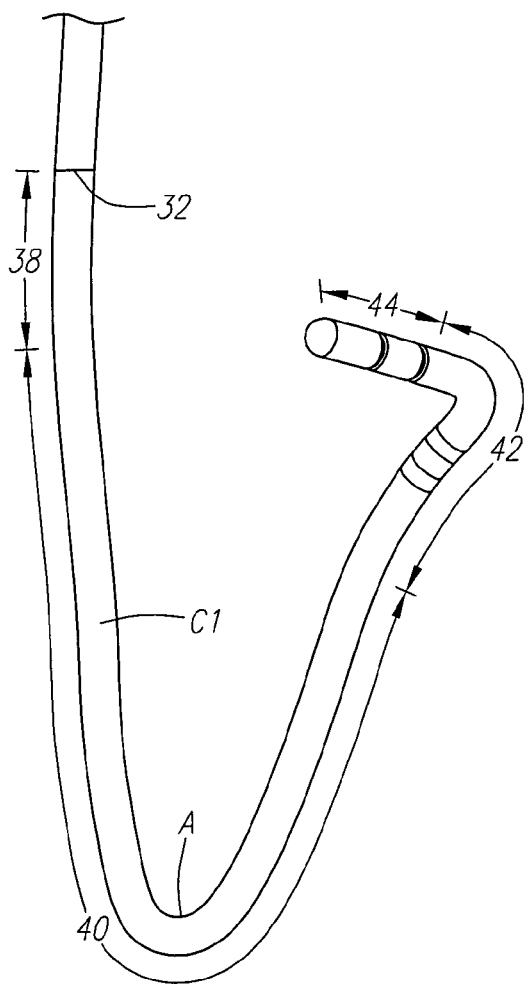
FIG. 3 is another perspective view of the distal end of the ablation/mapping catheter of FIG. 2.

As best shown in FIGS. 2 and 3, the distal member 30 has four geometrically distinct sections: (1) a shaft transition section 38 that distally extends from the proximal member 28; (2) a proximal section 40 that distally extends from the shaft transition section 38 and serves to provide an anchoring point within the vessel ostium around which the ablative/mapping elements 22, 24 can be positioned; (3) an intermediate section 42 that distally extends from the proximal section 40 and serves to properly locate the distal section 44 relative to the tissue outside of the vessel ostium; and (4) a distal section 44 that distally extends from the intermediate section 42 and serves to carry the tissue ablative element 22. The distal member 30 is uniquely shaped to perform the aforementioned functions.

In particular, referring further to FIGS. 2-6, the shaft transition section 38 is pre-shaped into a straight geometry. In the illustrated embodiment, the proximal member 28 and transition section 38 of the distal member 30 are collinear (i.e., the proximal member 28 and transition section 38 are not angled relative to each other). In this manner, bending forces that would otherwise be applied at the interface 32 between the proximal and distal members 28, 30 are minimized, thereby allowing more axial force to be applied to the ablation/mapping catheter 12 without collapsing the distal member 30 onto the proximal member 28 when proximal resistance is applied to the distal member 30. Such proximal resistance would typically be encountered within placing the distal member 30 within the ostium of a vessel, as will be described in further detail below.

Figure 4:
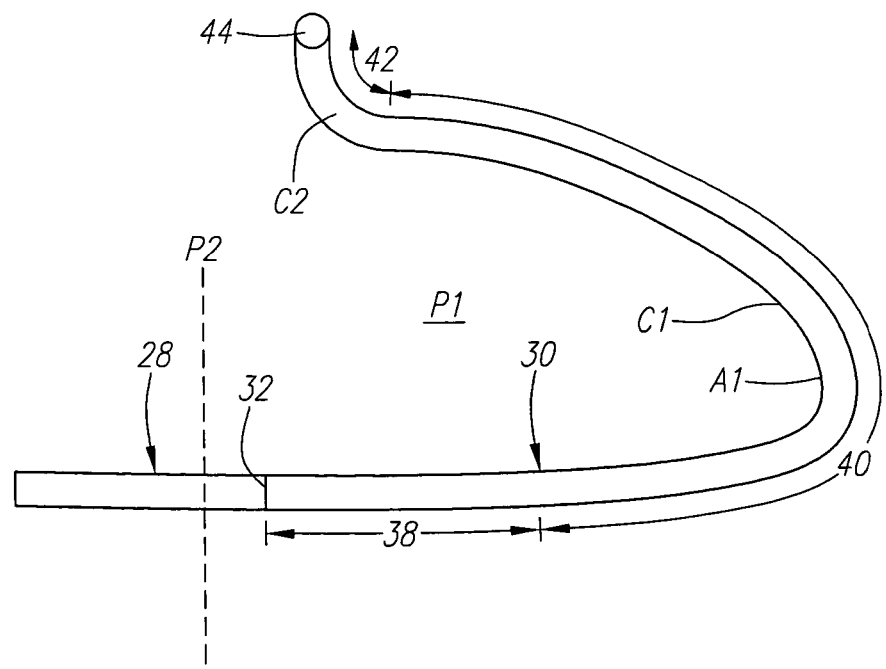
FIG. 4 is a plan view of the distal end of the ablation/mapping catheter of FIG. 2.
Figure 5:
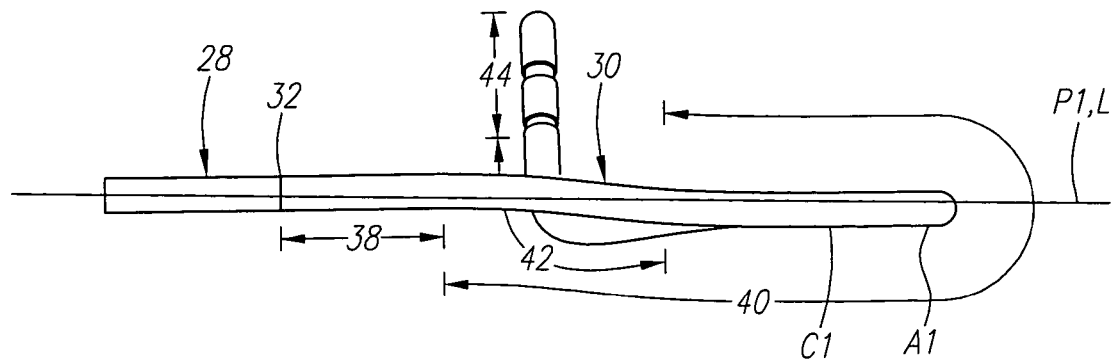
FIG. 5 is a profile view of the distal end of the ablation/mapping catheter of FIG. 2.

As best illustrated in FIG. 4, the proximal section 40 is configured to be internally actuated from a straight geometry to form a simple curve C1 (i.e., a curve that lies in a single plane, and in this case, plane P1 as illustrated in FIG. 5) in the absence of an external force (e.g., the force of gravity and the compressive force otherwise applied to the distal member 30 by the guide sheath 14). In the embodiment illustrated in FIG. 1, internal actuation of the proximal section 40 is accomplished by pre-shaping the proximal section 40 into the desired curve, and in particular, by incorporating the pre-shaped center support 46 into the distal member 30, as discussed above. The particular unconstrained shape of the proximal section 40 is such that an apex A1 of the simple curve C1 can be conveniently inserted into the ostium O of an anatomical vessel V, as illustrated in FIGS. 7 and 8. Preferably, to facilitate this insertion, the simple curve C1 bends more than 70 degrees, preferably more than 90 degrees, and more preferably, greater than 135 degrees. However, the bend of the simple curve C1 is preferably not so great that the proximal section 40 does not intersect itself.

The intermediate section 42 is configured to be internally actuated from a straight geometry to form a complex curve (i.e., a curve that can be projected onto more than one plane) in the absence of an external force, and in particular, a compressive force. In the embodiment illustrated in FIG. 1, internal actuation of the intermediate section 42 is accomplished by pre-shaping the intermediate section 42 into the desired curve, as will be described in further detail below. The particular unconstrained shape of the intermediate section 42, is such, that it bends opposite to and out-of-plane with the simple curve C1. That is, the complex curve has a proximal curve C2 that, when projected onto the plane P1 (see FIG. 4), bends opposite to the simple curve C1, and a distal curve C3 that, when projected on a plane P2 that is perpendicular to the longitudinal axis L of the proximal member 28 (see FIG. 6), bends out of the plane P1. As will be described in further detail below, the proximal projected curve C2 serves to properly locate the distal section 44 into contact with the tissue located outside of the vessel ostium O, as illustrated in FIG. 7. The distal projected curve C3 serves to place the distal section 44 into a non-radial relationship (i.e., oblique or tangential) with the vessel ostium O, as illustrated in FIG. 8.

In the illustrated embodiment, the proximal projected curve C2 has a 90 degree bend, so that the distal section 44 can be placed firmly against the tissue surrounding the vessel ostium O, as illustrated in FIG. 7. Alternatively, the proximal projected curve C2 can have a greater than 90 degree bend to maximize the contact between the distal section 44 and the surrounding tissue, but preferably does not exceed 135 degrees to minimize any chance that the distal section 44 may enter into the vessel ostium O. In the illustrated embodiment, the distal projected curve C3 has a 90 degree bend, so that the distal section 44 is arranged tangentially relative to the vessel ostium O, as illustrated in FIG. 8. Alternatively, the distal projected curve C3 may have any bend that arranges the distal section 44 obliquely relative to the vessel ostium, but preferably falls within the range of 60 to 120 degrees, so that the oblique relationship of the distal section 44 falls within the range of −30 to 30 degrees from the tangent. In this manner, the distal section 44 spans as much of the tissue surrounding the vessel ostium O as possible.

As best illustrated in FIGS. 5 and 6, the distal section 44 is pre-shaped into a straight geometry. Alternatively, the distal section 44 may be pre-shaped into a curved geometry. In this case, the distal section 44 preferably forms a simple curve C4 having an apex A2 that points away from the longitudinal axis L1 of the proximal member 28, as illustrated in FIG. 9. In this manner, the shape of the distal section 44 will conform better with the perimeter of the vessel ostium O. Notably, such a configuration will form the ablative element 22 into a curvilinear ablative element (as opposed to a linear ablative element that would be formed when mounted on a catheter section that is straight).

Figure 14:
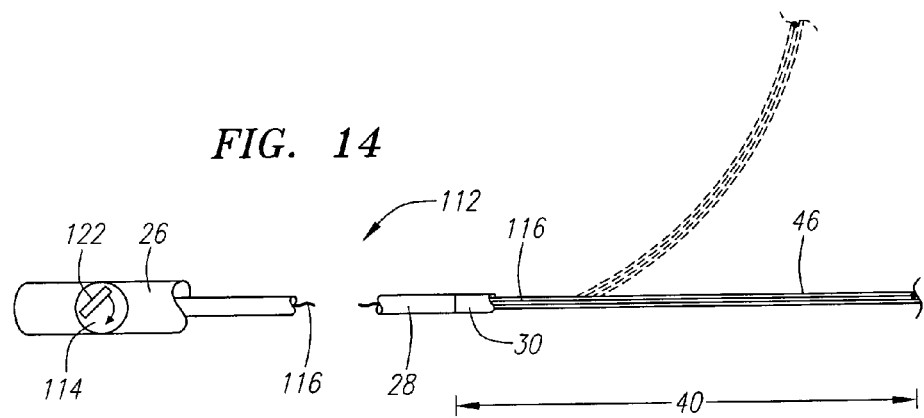
FIG. 14 is a partially cutaway view of the distal end of an alternative ablation/mapping catheter than can be used in the tissue ablation system of FIG. 1, particularly showing another means for internally actuating the catheter.

Alternatively, rather than pre-shaping the proximal section 40 of the distal member 30, a steering mechanism may be used to bend the proximal section 40. In particular, FIG. 14 illustrates an ablation/mapping catheter 112 that is similar to the previously described catheter 12, with the exception that a steering mechanism is used to transform the proximal section 40 of the distal member 28 from its straight geometry into its curved geometry, as illustrated in FIG. 14. In particular, the catheter 112 comprises a steering mechanism 114 that is incorporated into the handle 26, and a steering wire 116 with its proximal end attached to the steering mechanism 114 and its distal end connected to the center support 46 at the interface between the proximal and intermediate sections 40, 42 of the distal member 30. The steering wire 116 is attached to the side of the center support 46 that faces the direction in which the proximal section 40 of the distal member 30 is configured to curve or bend (as shown in phantom).

Figure 15:
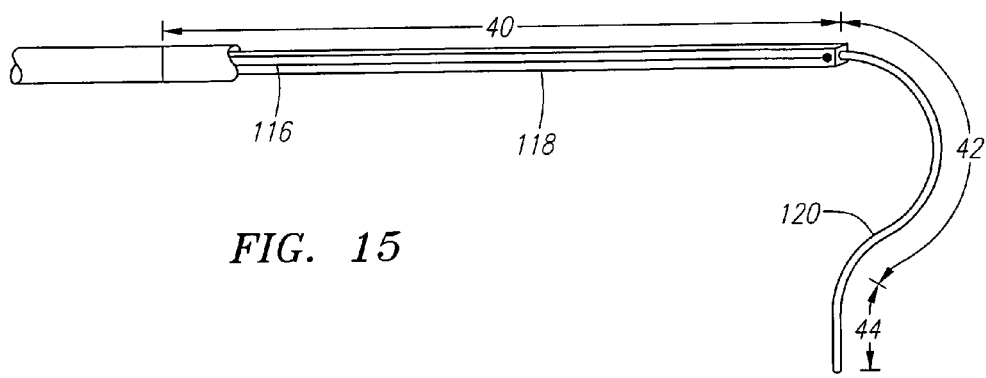
FIG. 15 is a partially cutaway view of the distal end of another alternative ablation/mapping catheter than can be used in the tissue ablation system of FIG. 1, particularly showing still another means for internally actuating the catheter.

Alternatively, as illustrated in FIG. 15, a center support 118 that terminates at the interface between the proximal and intermediate sections 40, 42 of the distal member 30 can be used, in which case, a resilient wire 120, which is suitably mounted to the distal end of the center support 46, can be used to pre-shape the intermediate/distal sections 42, 44, as described above. In this case, the center support 46 can be designed to provide the catheter 112 with steering capability independent of the design constraints imposed by pre-shaping the intermediate/distal sections 42, 44.

In any event, the steering mechanism 114 comprises a rotatable steering lever 122, which when rotated in one direction, tensions the steering wire 116, thereby flexing the center support 46, and thus the proximal section 40 of the distal member 30, into the desired curve (shown in phantom). In contrast, rotation of the steering lever 122 in the opposite direction provides slack in the steering wire 116, thereby allowing the resiliency of the center support 46 to flex the proximal section 40 of the distal member 30 back into a straight geometry. Alternatively, the steering lever may be of the sliding type, wherein rearward movement of the steering lever flexes the center support 46, and thus the proximal section 40 of the distal member 30, into the desired curve, and forward movement of the steering lever allows the resiliency of the center support 46 to flex the proximal section 40 of the distal member 30 back into the straight geometry. Steering mechanisms for bending the distal ends of the catheters are well known in the prior art, and thus need not be described in further detail.

As briefly discussed above with respect to FIG. 1, the ablation/mapping catheter 12 comprises a tissue ablative element 22, which is mounted on the distal member 30 of the catheter body 20. In the illustrated embodiment, the ablative element 22 takes the form of a linear electrode assembly that includes a cap electrode 48 mounted to the distal tip of the distal member 30 and a ring electrode 50 mounted on the distal section 44 of the distal member 30 just proximal to the cap electrode 48.

Notably, the split nature of the ablative element 22 provides selective monopolar and bipolar functionality to the catheter 12. That is, one or both of the tip/ring electrodes 48, 50 can be configured as one pole of a monopolar arrangement, so that ablation energy emitted by one or both of the electrodes 48, 50 is returned through an indifferent patch electrode (not shown) externally attached to the skin of the patient; or the tip/ring electrodes 48, 50 can be configured as two poles of a bipolar arrangement, in which energy emitted by one of the tip/ring electrodes 48, 50 is returned to the other electrode. In addition to serving as a selective unipolar/bipolar means of ablation, the tip/ring electrodes 48, 50 may also serve as a closely spaced high resolution pair of mapping electrodes. The combined length of the ablation electrodes 48, 50 is preferably about 6 mm to about 10 mm in length. In one embodiment, each ablation electrode is about 4 mm in length with 0.5 mm to 3.0 mm spacing, which will result in the creation of continuous lesion patterns in tissue when coagulation energy is applied simultaneously to the electrodes 48, 50.

The ablation electrodes 48, 50 may take the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. Any combination of the electrodes can also be in the form of helical ribbons or formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The ablation electrodes 48, 50 can alternatively comprise a porous material coating, which transmits coagulation energy through an electrified ionic medium. For example, as disclosed in U.S. Pat. No. 5,991,650, ablation electrodes may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

The ablation electrodes 48, 50 are electrically coupled to individual wires 52 (shown in FIGS. 10-12) to conduct ablation energy to them. The wires 52 are passed in conventional fashion through a lumen extending through the associated catheter body, where they are electrically coupled either directly to a connector (not shown) that is received in a port on the handle 26 or indirectly to the connector via a PC board (not shown) in the handle 26. The connector plugs into the RF generator 18 (shown in FIG. 1). Although ablation electrodes 48, 50 have been described as the operative elements that create the lesion, other operative elements, such as elements for chemical ablation, laser arrays, ultrasonic transducers, microwave electrodes, and ohmically heated hot wires, and such devices may be substituted for the electrodes 48, 50.

The ablation/mapping catheter 14 further comprises temperature sensors (not shown), such as thermocouples or thermistors, which may be located on, under, abutting the longitudinal end edges of, or in between, the electrodes 48, 50. In some embodiments, a reference thermocouple (not shown) may also be provided. For temperature control purposes, signals from the temperature sensors are transmitted to the RF generator 18 by way of wires (not shown) that are also connected to the aforementioned PC board in the handle 26. Suitable temperature sensors and controllers, which control power to electrodes based on a sensed temperature, are disclosed in U.S. Pat. Nos. 5,456,682, 5,582,609 and 5,755,715.

In the illustrated embodiment, the mapping element 24 takes the form of a pair of ring electrodes 52, 54 that are mounted on the intermediate section 42 of the distal member 30. Optionally, additional pairs of ring electrodes may be located along the distal member 30. The mapping electrodes 52, 54 are composed of a solid, electrically conducting material, like platinum or gold, attached about the catheter body 20. Alternatively, the mapping electrodes 52, 54 can be formed by coating the exterior surface of the catheter body 20 with an electrically conducting material, like platinum or gold. The coating can be applied using sputtering, ion beam deposition, or equivalent techniques. The mapping electrodes 52, 54 can have suitable lengths, such as between 0.5 and 5 mm. In use, the mapping electrodes 52, 54 sense electrical events in myocardial tissue for the creation of electrograms, and are electrically coupled to the mapping processor 16 (shown in FIG. 1). A signal wire 54 (shown in FIGS. 10-12) is electrically coupled to each mapping electrode 52, 54. The wires 54 extend through the catheter body 20 into an external multiple pin connector (not shown) located on the handle 26, which electrically couples the mapping electrodes 52, 54 to the mapping processor 16.

Having described the structure of the treatment system 10, its operation in creating a circumferential lesion within the ostium O of a pulmonary vein PV, thereby electrically isolating arrhythmia causing substrates within the pulmonary vein PV from the left atrium LA of the heart H, will now be described with reference to FIGS. 16A-16G. It should be noted that the views of the heart H and other interior regions of the body described herein are not intended to be anatomically accurate in every detail. The figures show anatomic details in diagrammatic form as necessary to show the features of the embodiment described herein.

Figure 16A:
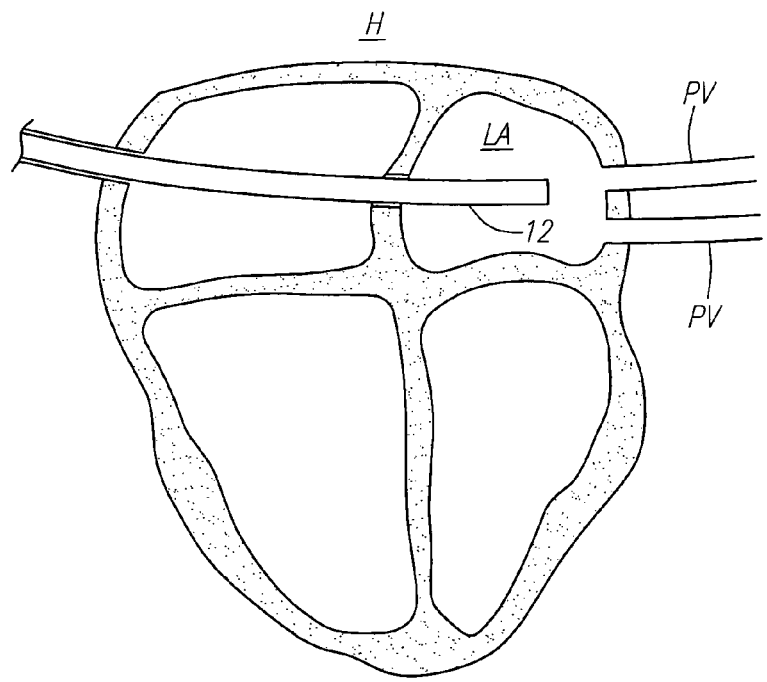

First, the guide sheath 12 is introduced into the left atrium LA of the heart H, so that the distal end of the sheath 12 is adjacent a selected pulmonary vein PV (FIG. 16A). Introduction of the guide sheath 12 within the left atrium LA can be accomplished using a conventional vascular introducer retrograde through the aortic and mitral valves, or can use a transseptal approach from the right atrium, as illustrated in FIG. 16A. A guide catheter or guide wire (not shown) may be used in association with the guide sheath 12 to aid in directing the guide sheath 12 through the appropriate artery toward the heart H.

Figure 16B:
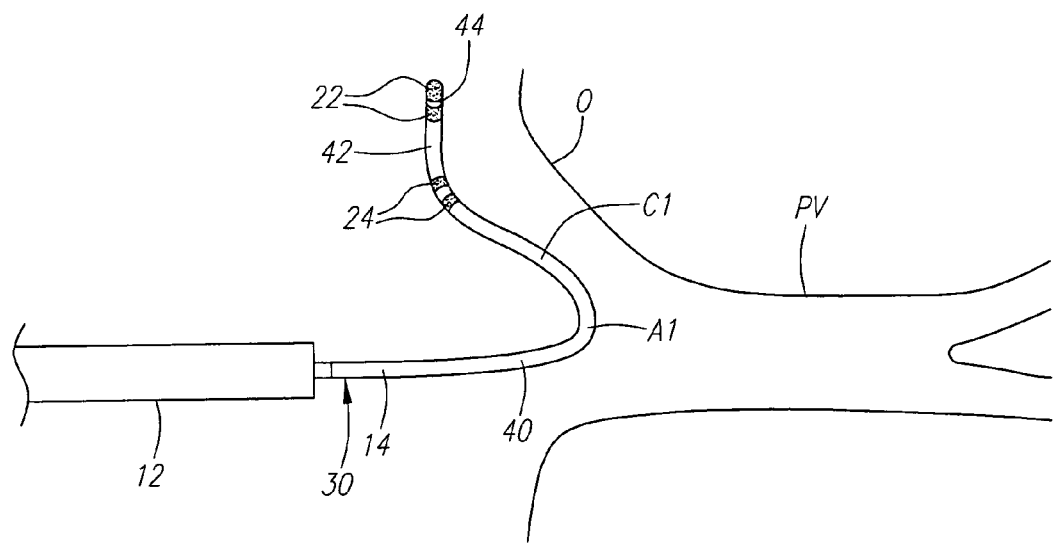
Figures 1, 16C:
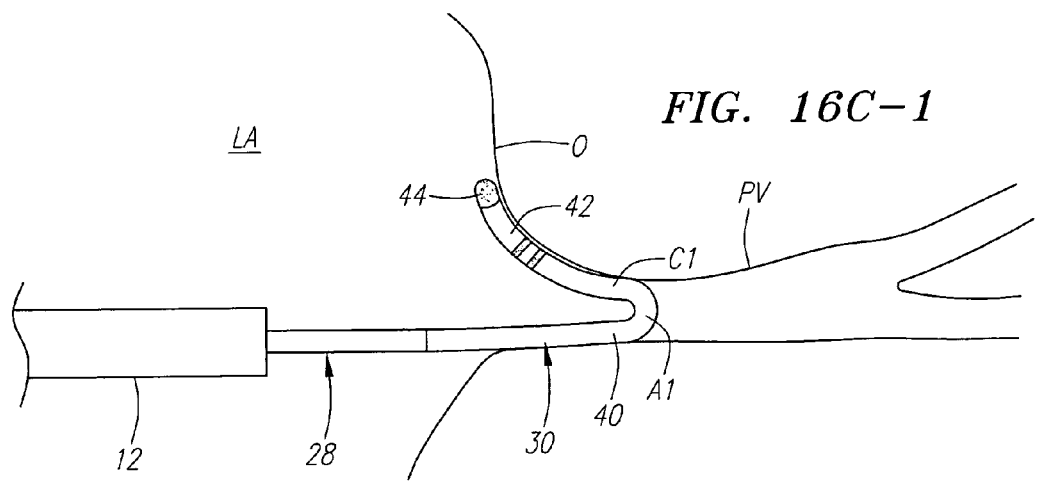
Figures 2, 16C:
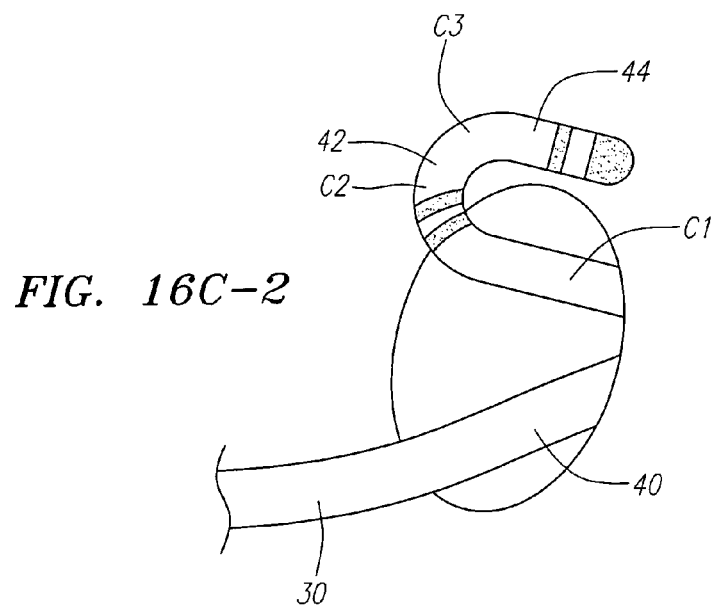

Once the distal end of the guide sheath 12 is properly placed, the ablation/mapping catheter 14 is introduced through the guide sheath 12 until the distal member 30 is deployed from the guide sheath 12 (FIG. 16B). As can be seen, the curvable section of the catheter body 20, and in particular the proximal section 40, is automatically placed into its curved geometry (i.e., it forms the curve C1 with the apex A1) due to its pre-shaped nature. Alternatively, if the catheter 12 is steerable, the steering mechanism can be manipulated to placed the proximal section 40 into its curved geometry. The apex A1 of the curve C1 is then inserted into the ostium O of the pulmonary vein PV until the intermediate/distal sections 42, 44, and in particular, the ablative element 22 and mapping element 24 are placed into contact with tissue sites adjacent the ostium O (FIGS. 16C-1 and 16C-2). As can be seen, the curve C2 of the intermediate section 42 directs the distal section 44 towards the tissue outside of the ostium O, and the curve C3 of the intermediate section 42 places the distal section 44 in a non-radial relationship, and specifically a tangential relationship, with the ostium O.

Notably, the resiliency of the intermediate section 42 of the distal member 30 places the ablative/mapping elements 22, 24 in firm and stable contact with the tissue sites. Also, because the distal member 30 comprises a radio-opaque substance, the relative locations of the portions of the proximal section 40 on either side of the apex A1 will provide the operator with an indication of the extent to which the curve C1 is placed within the ostium O, and thus, an indication of the location of the ablative/mapping elements 22, 24 relative to the ostium O. That is, the angle between the proximal section portions decreases as the depth of the curve C1 within the ostium O increases. Knowledge of this depth provides an indication of the location of the ablative/mapping elements 22, 24 relative to the ostium O.

Once the ablation/mapping elements 22, 24 are firmly and stably in contact with the tissue sites, the mapping processor 16 (shown in FIG. 1) is operated in order to obtain and record ECG signals from the ostium, with the ablative element 22 serving as a mapping element to measure ECG signals outside of the ostium O, and the mapping element 24 serving to measure ECG signals inside of the ostium O. As described below, these ECG signals will be compared with the ECG signals obtained subsequent to an ablation procedure in order to determine if the resultant lesion has successfully electrically isolated the arrhythmia causing substrates from the left atrium LA of the heart H. Additional tissue sites can be mapped by rotating the curve C1 within the ostium O about the apex A1 to place the ablation/mapping elements 22, 24 in contact with other tissue sites, and operating the mapping processor 16.

Once the pre-ablation ECG signals have been obtained and recorded, the ablative element 22 is placed in contact with a first tissue site S1 (FIG. 16D). This can be accomplished simply by leaving the curve C1 in place after mapping has been completed or by rotating the curve C1 within the ostium O about the apex A1 to place the ablative element 22 into contact with a different tissue site at which the last mapping procedure was performed. The RF generator 18 (shown in FIG. 1) is then operated in order to convey RF energy to the ablative element 22 (either in the monopolar or bipolar mode), thereby creating a linear lesion L1 (FIG. 16E). As can be seen, the linear lesion L1 is tangential to the perimeter of the ostium O, thereby maximizing the span of the lesion L1 about the ostium O and the effectiveness of the lesion L1 in blocking the errant electrical pathways from the pulmonary vein PV. Alternatively, the linear lesion L1 may be somewhat oblique to the perimeter of the ostium O, but preferably does not deviate more than 30 degrees from the tangent to the ostium O.

Next, the curve C1 is again rotated within the ostium O about the apex A1 to place the ablative element 22 into contact with a second tissue site S2 (FIG. 16F). Then, the RF generator 18 is operated in order to convey RF energy to the ablative element 22, thereby creating another linear lesion L2 (FIG. 16G). As can be seen, the linear lesion L2, like the linear lesion L1, is tangential to the perimeter of the ostium O, thereby maximizing the span of the lesion L2 about the ostium O and the effectiveness of the lesion L2 in blocking the errant electrical pathways from the pulmonary vein PV. In the illustrated method, the location of the second tissue site S2 is selected such that the linear lesions L1 and L2 form a continuous lesion. This ablation process is repeated until the entire ostium O is encircled with a circumferential lesion. Alternatively, if the locations of the arrhythmia causing substrates are known, the tissue sites S can be selected, such that discrete linear lesions L are formed around the ostium O at strategic locations.

As can be appreciated, formation of the lesions L around the ostium O can be more controlled and predefined, since movement of the ablative element 22 is limited to a circle having a point at the apex A1 of the curve C1. This can be contrast with the previous "free-hand" approach where movement of the ablative element 22 is unlimited and difficult to control. In addition, the unique design of the distal member 30 ensures that the ablative element 22 is kept out of the PV where irreparable damage can be caused.

After the lesion has been created, the mapping processor 16 is again operated to obtain and record ECG signals from the PV. These post-ablation ECG signals are compared to the pre-ablation ECG signals to determine whether the circumferential lesion has completely isolated the arrhythmia causing substrates in the pulmonary vein PV from the LA of the heart H. Once proper ablation has been confirmed, the guide sheath 12 and ablation/mapping catheter 14 are removed from the patient's body, or alternatively, are used to create a circumferential lesion within another pulmonary vein.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A catheter, comprising:
    an elongated flexible integrated catheter body including:
        a proximal shaft portion having a longitudinal axis,
        a distal shaft portion having a proximal section configured to be internally actuated to form a simple curve that bends more than 70 degrees, an intermediate section pre-shaped to form a complex curve, and a distal section, wherein the simple curve lies in a single plane, and the complex curve can be projected onto the single plane and another plane orthogonal to the single plane, the complex curve, when projected onto the single plane, bending in a direction opposite to the direction that the simple curve bends; and
    at least one operative element carried by the distal section.
2. The catheter of claim 1, wherein the at least one operative element comprises a tissue ablative element.
3. The catheter of claim 2, wherein the ablative element is a linear tissue ablative element.
4. The catheter of claim 1, wherein the at least one operative element comprises a diagnostic element.
5. The catheter of claim 1, further comprising a steering mechanism operable to internally actuate the proximal section to form the simple curve.
6. The catheter of claim 1, wherein the proximal section is pre-shaped to form the simple curve in the absence of an external force.
7. The catheter of claim 1, wherein the simple curve is eccentric and has a radius of curvature that is smallest at an apex of the simple curve.
8. The catheter of claim 1, wherein the simple curve bends more than 90°.
9. The catheter of claim 1, wherein the simple curve bends more than 135°.
10. The catheter of claim 1, wherein the simple curve bends less than 180°.
11. The catheter of claim 1, wherein the proximal section is radio-opaque.
12. The catheter of claim 1, wherein the complex curve has a proximal curve that, when projected onto the single plane, bends at least 90°.
13. The catheter of claim 1, wherein the complex curve has a proximal curve that, when projected onto the single plane, bends in the range of 90° to 135°.
14. The catheter of claim 1, wherein the other plane is perpendicular to the longitudinal axis, and the complex curve has a distal curve that, when projected onto other plane, bends in the range of 60° to 120°.
15. The catheter of claim 1, wherein the other plane is perpendicular to the longitudinal axis, and the complex curve has a distal curve that, when projected onto other plane, bends approximately 90°.
16. The catheter of claim 1, wherein the distal section forms a distal tip of the catheter body.
17. The catheter of claim 1, wherein the distal section is straight.
18. The catheter of claim 1, wherein the distal section is pre-shaped to form a simple curve having an apex that points away from a longitudinal axis of the proximal shaft portion.
19. The catheter of claim 1, wherein the smallest radius of curvature of the simple curve is within the range of 1.25 to 2.50 centimeters, and the smallest radius of curvature of the complex curve is within the range of 1.25 to 3.75 centimeters.
20. The catheter of claim 1, wherein the proximal section has a length within the range of 2.50 to 6.50 centimeters, the intermediate section has a length within the range of 0.50 to 2.00 centimeters, and distal section has a length within the range of 0.50 to 2.00 centimeters.
21. The catheter of claim 1, wherein the distal shaft portion includes a substantially straight shaft transition section between the proximal shaft portion and the proximal section of the distal shaft portion.
22. The catheter of claim 21, wherein the proximal shaft portion and the shaft transition section are collinear.
23. A method of performing a medical procedure adjacent an ostium of a vessel using the catheter of claim 1, comprising:
    inserting an apex of the simple curve into the vessel ostium to place the at least one operative element in contact with a first tissue site adjacent the vessel ostium; and
    performing the medical procedure on the first tissue site with the at least one operative element.
24. The method of claim 23, further comprising:
    rotating the simple curve within the vessel ostium about the apex to place the operative element in contact with a second tissue site adjacent the vessel ostium; and performing the medical procedure on the second tissue site with the at least one operative element.

25. The method of claim 23, wherein the at least one operative element comprises an ablative element, and performing the medical procedure comprises forming a lesion at the first tissue site with the ablative element.

26. The catheter of claim 1, wherein the proximal section is configured to be internally actuated from a straight geometry to the simple curve.

27. A catheter, comprising:
   an elongated flexible integrated catheter body including:
      a proximal shaft portion having a longitudinal axis,
      a distal shaft portion having a proximal section configured to be internally actuated to form a simple curve with an apex that can be inserted into an ostium of an anatomical vessel, an intermediate section pre-shaped to form a curve that bends opposite the simple curve, and a distal section configured to be placed into a non-radial relationship with the vessel ostium merely by the insertion of the apex of the simple curve into the vessel ostium; and
   at least one operative element carried by the distal section, and configured to be placed firmly in contact with tissue adjacent the vessel ostium when the apex of the simple curve is inserted into the vessel ostium.

28. The catheter of claim 27, wherein the at least one operative element comprises a tissue ablative element.

29. The catheter of claim 28, wherein the ablative element is a linear or curvilinear tissue ablative element.

30. The catheter of claim 27, wherein the at least one operative element comprises a diagnostic element.

31. The catheter of claim 27, further comprising a steering mechanism operable to internally actuate the proximal section to form the simple curve.

32. The catheter of claim 27, wherein the proximal section is pre-shaped to form the simple curve in the absence of an external force.

33. The catheter of claim 27, wherein the proximal section is radio-opaque.

34. The catheter of claim 27, wherein the distal section forms a distal tip of the catheter body.

35. The catheter of claim 27, wherein the non-radial relationship is a substantially tangential relationship.

36. The catheter of claim 27, wherein the non-radial relationship is an oblique relationship that falls within the range of −30° and 30° from the tangent.

37. The catheter of claim 27, wherein the vessel is a pulmonary vein in an adult human.

38. A method of performing a medical procedure adjacent an ostium of a vessel using the catheter of claim 27, comprising:
   inserting the apex of the simple curve into the vessel ostium of a vessel to place the at least one operative element in contact with a first tissue site adjacent the vessel ostium while the distal section is placed into the non-radial relationship with the vessel ostium; and
   performing the medical procedure on the first tissue site with the at least one operative element.

39. The method of claim 38, further comprising:
   rotating the curve within the vessel ostium about the apex to place the operative element in contact with a second tissue site adjacent the vessel ostium; and
   performing the medical procedure on the second tissue site with the at least one operative element.

40. The method of claim 38, wherein the at least one operative element comprises an ablative element, and performing the medical procedure comprises forming a lesion at the first tissue site with the ablative element.

\* \* \* \* \*